United States Patent [19]

Stradal et al.

[11] Patent Number: 5,393,542
[45] Date of Patent: Feb. 28, 1995

[54] PROCESS FOR PRODUCING HYDROXYACETALDEHYDE

[75] Inventors: John A. Stradal; Gary L. Underwood, both of Manitowoc, Wis.

[73] Assignee: Red Arrow Products Company Inc., Manitowoc, Wis.

[21] Appl. No.: 92,475

[22] Filed: Jul. 16, 1993

Related U.S. Application Data

[60] Division of Ser. No. 866,567, Apr. 10, 1992, Pat. No. 5,252,188, which is a continuation-in-part of Ser. No. 675,145, Mar. 26, 1991, abandoned, which is a continuation-in-part of Ser. No. 535,735, Jun. 8, 1990, abandoned, which is a continuation-in-part of Ser. No. 498,849, Mar. 26, 1990, abandoned.

[51] Int. Cl.$^6$ .............................................. A23L 1/27
[52] U.S. Cl. ................................. 426/241; 426/265; 426/268
[58] Field of Search ............... 426/268, 533, 650, 241, 426/265; 568/465, 486, 492, 496

[56] References Cited

U.S. PATENT DOCUMENTS

| | | |
|---|---|---|
| 3,106,473 | 10/1963 | Hollenbeck . |
| 3,330,669 | 7/1967 | Hollenbeck . |
| 3,505,407 | 4/1970 | Cavitt . |
| 3,806,609 | 4/1974 | Goblik et al. . |
| 4,359,481 | 11/1982 | Smits et al. . |
| 4,431,032 | 2/1984 | Nicholson . |
| 4,431,033 | 2/1984 | Nicholson . |
| 4,496,595 | 1/1985 | Nicholson . |
| 4,504,500 | 3/1985 | Schneck et al. . |
| 4,504,501 | 3/1985 | Nicholson . |
| 4,504,507 | 3/1985 | Nicholson . |
| 4,505,939 | 3/1985 | Chiu . |
| 4,525,397 | 6/1985 | Chiu . |
| 4,657,765 | 4/1987 | Nicholson et al. . |
| 4,717,576 | 6/1988 | Nicholson et al. . |
| 4,876,108 | 10/1989 | Underwood et al. . |
| 4,883,676 | 11/1989 | Sophianopoulos et al. . |
| 4,938,868 | 7/1990 | Nelson . |
| 4,994,297 | 2/1991 | Underwood et al. . |

FOREIGN PATENT DOCUMENTS

| | | |
|---|---|---|
| 932686 | 8/1973 | Canada . |
| 1137637 | 12/1968 | United Kingdom .. |
| WO8800935 | 2/1988 | WIPO . |

OTHER PUBLICATIONS

Arseneu et al., "A Study of Reaction Mechanisms by DSC and TG," *Thermal Analysis*, vol. 3, Proceedings Third ICTA Davos, 1971, pp. 319–326.

Bailey, "Inhibition of Warmed–Over Flavor, With Emphasis on Maillard Reaction Products," *Food Technology*, Jun. 1988, pp. 123–126.

Beaumont et al., "Influence of Physical and Chemical Parameters on Wood Pyrolysis," *Ind. Eng. Chem. Process Des. Dev.*, vol. 23, No. 4, 1984, pp. 637–641.

(List continued on next page.)

*Primary Examiner*—Christopher Upton
*Attorney, Agent, or Firm*—Marshall, O'Toole, Gerstein, Murray & Borun

[57] ABSTRACT

This invention provides a process for producing crystalline hydroxyacetaldehyde precipitated from a complex mixture of products provided by the pyrolysis of a carbohydrate-containing feedstock. The method includes distilling a first condensate under reduced pressure to give a second condensate which is enriched in hydroxyacetaldehyde; combining the second condensate with a solvent to give a homogeneous solution; precipitating hydroxyacetaldehyde from the solution; and separating the precipitated hydroxyacetaldehyde from the solution.

Aqueous solutions of hydroxyacetaldehyde are useful for browning foodstuffs and for producing flavors by contacting the hydroxyacetaldehyde with ammonia or amines.

In addition, hydroxyacetaldehyde may be used to make an artificial tanning product containing a suitable topical vehicle and an amount of hydroxyacetaldehyde suitable to impart a brown color to skin.

17 Claims, 2 Drawing Sheets

OTHER PUBLICATIONS

Berg et al., "Characterization of Solids Mixing in an Ultra-Rapid Fluidized Reactor," Paper presented in London, Ontario, Canada, May 12–15, 1986.

Berg et al., "Rapid Mixing Studies Between Transported Solids in an Ultra-Rapid Fluidized Reactor," Powder & Bulk Solids Conference, Rosemont, Ill., May 1985.

Bryne et al., "The Pyrolysis of Cellulose and the Action of Flame Retardants," *J. Appl. Chem.*, vol. 16, Mar. 1966, pp. 81–88.

Collins et al., "Nuclear Magnetic Resonance Spectra of Glycolaldehyde," *J. Chem. Soc. (B)*, 1971, pp. 1352–1355.

Evans et al., "New Approaches to the Study of Cellulose Pyrolysis," *American Chemical Society*, vol. 36, No. 2, 1991, pp. 714–724.

Fenton et al., "Crystalline Clycollic Aldehyde," University Chemical Laboratory, Cambridge.

Glassner et al., "Gas Chromotographic Analysis of Products from Controlled Application of Heat to Paper and Levoglucosan," *Analytical Chemistry*, vol. 37, No. 4, Apr., 1965, pp. 525–527.

Graham et al., "Fast Pyrolysis of Biomass," *Journal of Analytical and Applied Pyrolysis* 6, (1984), pp. 95–135.

Jandera et al., "Ion–Exchange Chromatography of Aldehydes, Ketones, Ethers, Alcohols, Polyols and Saccharides," *Journal of Chromotography*, 98 (1974), pp. 55–104.

Kang et al., "Ketene Formation From the Pyrolysis of Carbohydrates," research paper, Philip Morris Research Center, Richmond, Va., pp. 261–273.

Maga et al., "Pyrazine Composition of Wood Smoke as Influenced by Wood Source and Smoke Generation Variables," *Flavour and Fragrance Journal*, vol. 1, 37–42, (1985).

Martinsson et al., "Partition Chromatography of Sugars on Ion–Exchange Resins," *J. Chromotog.*, 50 (1970) pp. 429–433.

Menard et al., "Characterization of Pyrolytic Liquids from Different Wood Conversion Processes," Fifth Canadian Bioenergy R&D Seminar, undated, pp. 418–434.

Michelsen et al., "Spectroscopic Studies of Glycolaldehyde," *J. Mol. Structure*, 4 (1969) 293–302.

Namiki et al., "A New Mechanism of the Maillard Reaction Involving Sugar Fragmentation and Free Radical Formation," *New Mechanism of Maillard Reaction*, pp. 21–46.

Namiki et al., "Formation of Novel Free Radical Products in an Early Stage of Maillard Reaction," *Prog. Fd. Nutr. Sci.*, vol. 5, pp. 81–91, 1981.

Pecina et al., "High–Performance Liquid Chromatographic Elution Behaviour of Alcohols, Aldehydes, Ketones, Organic Acids and Carbohydrates on a Strong Cation–Exchange Stationary Phase," *Journal of Chromatography*, 287 (1984) 245–258.

Piskorz et al., "On the Mechanism of the Rapid Pyrolysis of Cellulose," *Journal of Analytical and Applied Pyrolysis*, 9 (1986) 121–137.

Richards et al., "Influence of sodium chloride on volatile products formed by pyrolysis of cellulose: Identification of hydroxybenzenes and 1-hydroxy-2-propanone as major products," Carbohydrate Research, 117 (1983) 322–327.

Roy et al., "The Pyrolysis under Vacuum of Aspen Poplar," paper published in Fundamentals of Thermochemical Biomass Conversion, Edited by R. P. Overend, (1985) pp. 237–256.

Samuelson et al., "Partition Chromatograph of Mixtures Containing Polyols and Carbonyl Compounds (Including Sugars) on Ion Exchange Resins," *Acta Chem. Scand.*, 22 (1968) No. 4, 1252–1258.

Scott et al., Chemicals and Fuels from Biomass Flash Pyrolysis, Renewable Energy Branch, Energy Mines and Resource Canada, Ottawa, Canada pp. 12–78 (1988).

Scott et al., "Sugars From Business Cellulose by a Thermal Conversion Process," paper published in Energy From Biomass and Wastes XIII Edited by Donald L. Klass, presented at conference in New Orleans Feb. 13–17, 1989, pp. 1349–1363.

Shafizadeh, "Industrial Pyrolysis of Cellulosic Materials," *Applied Polymer Symposium*, No. 28, 153–174 (1975).

Shafizadeh et al., "Pyrolysis of Cellulose," *Carbohydrate Research*, 29 (1973) 113–122.

Stassinopoulou et al., "A Study of the Dimeric Structures of Glycolaldehyde Solutions by NMR," *Tetrahedron.*, vol. 28, pp. 1257–1263 (1972).

Wodley, "Pyrolysis Products of Untreated and Flame Retardant-Treated $\alpha$-Cellulose and Levoglucosan," Naval Radiological Defense Laboratory, pp. 835–851.

FIG.1

PROCESS FOR PRODUCING HYDROXYACETALDEHYDE

CROSS-REFERENCE TO RELATED APPLICATIONS

This application is a divisional of U.S. patent application Ser. No. 07/866,567 filed Apr. 10, 1992, now U.S. Pat. No. 5,252,188, which is a continuation-in-part of U.S. patent application Ser. No. 07/675,145, filed Mar. 26, 1991, abandoned, which is a continuation-in-part of U.S. patent application Ser. No. 07/535,735, filed Jun. 8 1990, which is a continuation-in-part of U.S. patent application Ser. No. 07/498,849, filed Mar. 26, 1990, both abandoned.

BACKGROUND OF THE INVENTION

This invention relates generally to a process to produce hydroxyacetaldehyde from a pyrolyzed carbohydrate-containing feedstock and, more specifically, to a process to produce hydroxyacetaldehyde from a water soluble fraction of pyrolysis products obtained from a pyrolyzed carbohydrate-containing feedstock such as wood, cellulose, sugars or starches. Aqueous solutions of hydroxyacetaldehyde are useful to color or brown proteinaceous materials and to produce natural flavors when combined with ammonia or amines.

Hydroxyacetaldehyde, HO—$CH_2$—CHO, (HAA) is the simplest aldehyde-alcohol or sugar. Fenton and Jackson, *J. Chem. Soc.*, 79:774 (1902) provide some physical characteristics and a synthesis of HAA. In the reported synthesis, an aqueous solution of dihydroxymaleic acid was heated and then distilled under reduced pressure. A viscous fraction that distilled at near 100° C. was collected and found to crystallize after cooling. Analysis of the crystalline material indicated the material was a crystalline dimer of HAA which was soluble in water or hot alcohol but only sparingly soluble in ether.

Subsequent studies suggest HAA may actually exist in solution in at least three different monomeric or dimeric forms and as a mixture of stereoisomers. See, for example, Michelsen and Klaboe, *J. of Molecular Structure*, 4:293–302 (1969), Collins and George, *J. Chem. Soc.* (B), 1352–1355 (1971), and Stassinopoulou and Zioudrou, *Tetrahedron*, 28:1257–1263 (1972).

Currently, commercially available HAA is sold as a crystalline dimer having a melting point of between 80°–90° C. depending on the stereoisomeric composition of the crystalline material.

HAA has also been identified in complex and variable mixtures of chemicals provided by the pyrolysis of carbohydrate-containing feedstocks. A typical carbohydrate pyrolysis mixture includes condensible liquids, non-condensible gases, and solids. The relative proportions of these materials are dependent on both the type of feed stock and the actual conditions of the pyrolysis. Many of the different chemicals actually identified in typical pyrolysis mixtures are present found in only trace or very small amounts. Other chemicals, however, are present in sufficient quantities to provide the possibility of isolating a particular chemical, such as hydroxyacetaldehyde, if economical separation schemes are available.

An efficient pyrolysis process for carbohydrate-containing feedstocks, especially wood, which gives improved overall HAA yields is described by Underwood et al., U.S. Pat. No. 4,876,108. Briefly, a primary pyrolysis liquid is condensed from wood pyrolysis vapors containing a mixture of water soluble and water insoluble organic compounds. A sufficient amount of water is added to the condensed liquid product to allow the separation of the water insoluble compounds from the water soluble compounds by extraction. The extractable water soluble compounds include a number carbonyl compounds such as sugars, ketones, aldehydes and acids. Identifiable compounds include oligosaccharides, cellobiosan, glucose, fructose, glyoxal, methylglyoxal, levoglucosan, 1,6-anhydroglucofuranose, HAA, formic acid, formaldehyde, acetic acid, ethylene glycol, acetol, acetaldehyde, and methanol. The bulk of the water soluble compounds probably originate from cellulose and hemicellulose present in wood. In total, over 300 compounds have been identified in wood pyrolysis mixtures which makes isolating a specific compound a formidable challenge.

According to Scott et al., "Chemicals and Fuels from Biomass Flash Pyrolysis," Renewable Energy Branch, Energy, Mines and Resources Canada, Ottawa, Canada (1988), the recovery of HAA from a water soluble fraction or from a primary pyrolysis liquid produced from wood presents some severe problems. Specifically, HAA is believed to be very reactive, and if heated, especially in basic solutions, rapidly undergoes condensation reactions.

In unsuccessful attempts to isolate HAA from the water soluble fraction of a wood pyrolysis product, Scott et al. evaluated a number of possible isolation methods including: making a volatile or crystalline derivative, steam distillation, adsorption, chromatographic separation, membrane separation, and metal chelation. The formation of HAA derivatives from the water soluble fraction of a wood pyrolysis mixture was not successful. Similarly, steam distillation was reported to be energy inefficient and yield poor mass recovery. Furthermore, HAA is a water miscible solid which is unsuitable for general steam distillation processes because of its high water solubility. Finally, adsorption and chromatographic methods were difficult or not practical because of the number of essentially similar compounds identified in typical pyrolysis mixtures.

Scott et al. concluded that the most promising approach might be selective adsorption of HAA on silicalite (silicalite is a hydrophobic small-pore high-silica content molecular sieve). However, both acetol and acetic acid, present in all the pyrolysis mixtures, are more efficiently adsorbed by silicalite than HAA. Therefore, even this adsorptive process would require significant refinement to be practical. Of the methods reported by Scott et al., the methods were too complex to be economically practiced on a commercial basis or not selective enough to provide HAA of sufficient purity for end-uses in the food or cosmetic industries.

The large number of compounds produced by pyrolyzing wood is a significant hindrance to the practical separation of useful quantities of any particular compound. The heat lability of HAA, in particular, increases the difficulty of its isolation. Other, less complex feedstocks, may produce somewhat less complex pyrolysis mixtures. For example, the fast pyrolysis of a carbohydrate-containing feedstock such as corn syrup provides a high browning water soluble composition that includes an increased percentage of HAA. Pyrolysis of a less complex carbohydrate-containing feedstocks, such as sugars, also gives multicomponent mixtures of water soluble compounds.

Pragmatically, for the separation of hydroxyacetaldehyde it is desirable to form pyrolysis mixtures having as few other compounds as is possible. Therefore, in certain applications it may be advantageous to pyrolyze a carbohydrate-containing feedstock which provides high yields of HAA with a relatively small number of other pyrolysis compounds.

In sum, a need exists for a process to produce HAA from mixtures obtained by pyrolyzing a carbohydrate-containing feedstock which is economical, efficient and amenable to scale-up. An efficient method of isolating HAA would allow for the use of aqueous HAA solutions as a coloring or browning agent in a foodstuff, as a product which may be used to flavor proteinaceous materials or in cosmetics.

SUMMARY OF THE INVENTION

The present invention provides a process to produce HAA from a multicomponent aqueous mixture which is obtained by pyrolyzing a carbohydrate-containing feedstock and collecting the condensible vaporous products produced by pyrolysis to give a first aqueous condensate. The first condensate is distilled under reduced pressure to give a second condensate having a reduced water content and the second condensate is combined with a sufficient amount of an organic solvent to give a homogenous solution containing at least 2% by weight HAA. The HAA present in the solution is precipitated and then separated from the HAA depleted liquid. A preferred first condensate is prepared by the fast pyrolysis of corn syrup to give a condensate containing about 16% HAA.

In the reduced pressure distillation, it is preferred to remove sufficient amounts of water from the first condensate in order to give a second condensate which will yield a homogenous solution which contains at least about 2% by weight HAA when combined with a suitable organic solvent. If the HAA concentration is too low, no HAA precipitates from the second condensate when combined with the organic solvent. If the water concentration is too high, even if the HAA is sufficient, combination with an organic solvent yields a mixture which separates into two phases. In this case, HAA is retained in the aqueous phase with other water soluble components and does not precipitate from the mixture.

In practicing the process of this invention a variety of carbohydrate-containing feedstocks may be used including wood, cellulose, sugars or starches. For example, any mono-, di-, tri- or polysaccharide which contains glucose or glucose monomers may be used to practice the present invention. Suitable saccharides include glucose, dextrose, invert sugar, lactose, malt syrup, molasses, starch hydrolysates and fractions therefore, sucrose, cellobiose, hemi-cellulose and cellulose. Wood also serves as a suitable feedstock although the presence of components in wood, in addition to cellulose, may provide an unduly complex pyrolysis mixture. Other suitable feedstock sources include plant derived material such as seed, leaf and fruit fibers as well as plant derived syrups and extracts.

In order to obtain the best yields of HAA in a first condensate, preferred feedstocks have a low nitrogen content. Nitrogen content is typically related to the presence of proteins or amines in a feedstock. If the nitrogen content is too high, the yield of HAA is reduced because the HAA generated during pyrolysis reacts with proteins and amines under typical pyrolysis conditions. For example, the nitrogen content of wood is generally less than about 0.5% and pyrolysis yields about 1% or more HAA, but the pyrolysis of mesquite, a wood having an extremely high nitrogen content, produces no measurable or a negligible amount of HAA in a pyrolysis condensate.

A first condensate useful to practice this invention may be obtained from carbohydrate-containing feedstock using pyrolysis and extraction methods which are well known in the liquid smoke art. For example, fast pyrolysis liquids, water soluble fractions of fast pyrolysis liquids, or concentrated conventional liquid smoke solutions having about 1–35% by weight HAA are all useful in practicing the invention. A preferred condensate is the concentrated water soluble extracts of a pyrolysis product produced by the fast pyrolysis of hardwood particles and a particularly preferred condensate is the concentrated water soluble extracts of produced by the fast pyrolysis of corn syrup.

Aqueous solutions containing HAA produced by the present invention are useful for browning a foodstuff by contacting the external surface of the foodstuff with a solution of HAA. Upon heating a treated foodstuff at typical cooking temperatures browning likely occurs as a result of HAA reacting with the foodstuff proteins. The browning process may also occur when the foodstuff is cooked in a microwave. Foodstuffs which may benefit by the presence of HAA to impart desired browning include cheeses, meats, sausages and encased food products, poultry and fish.

In addition, HAA solutions may be used to form natural flavors by reacting with ammonia, amines or amino acids or to inhibit warmed over flavors in meat products.

Suitable compositions of HAA may also be used to make a topical skin coloring or tanning product comprising a suitable topical vehicle and an amount of HAA suitable to impart a brown color to skin.

BRIEF DESCRIPTION OF THE DRAWINGS

Details of practicing a process of the invention are described by reference to the accompanying drawings in which.

DETAILED DESCRIPTION OF THE INVENTION

Figure 2:
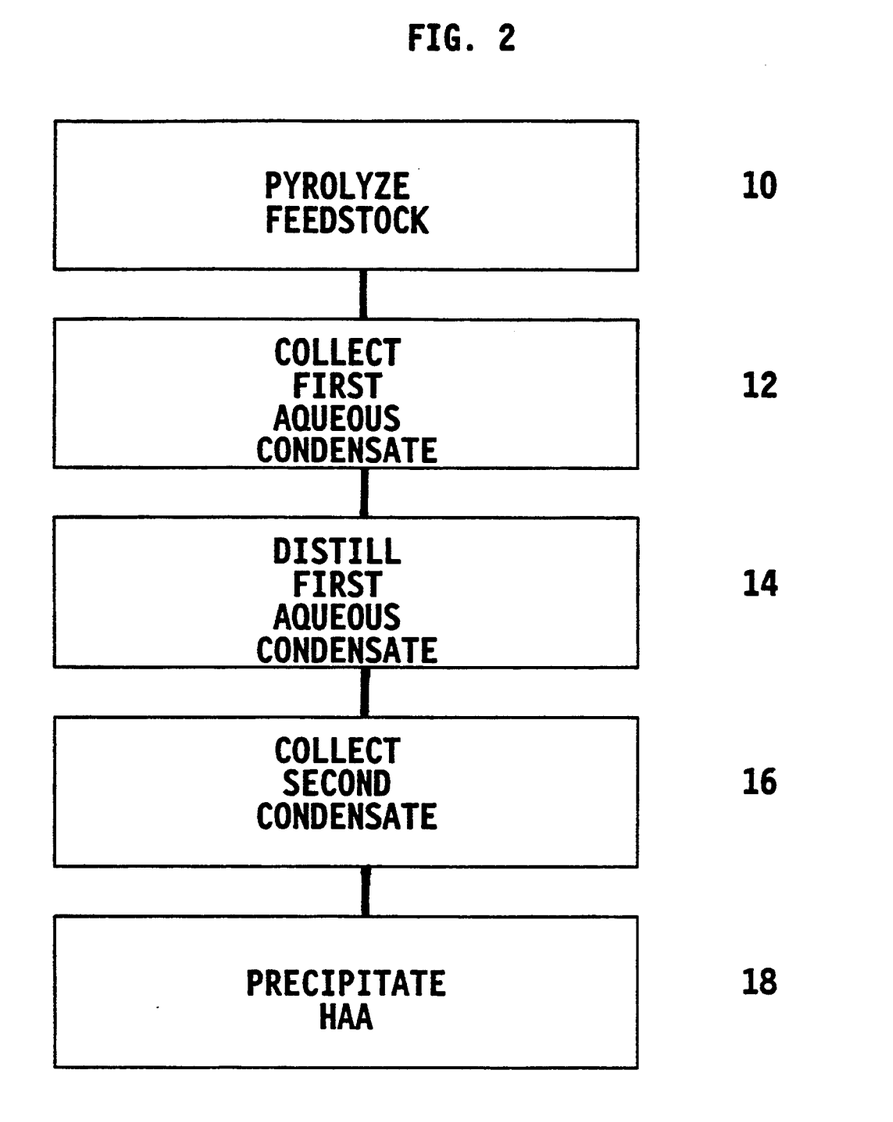

The present invention provides a process to produce HAA. The process includes pyrolysis of a suitable feedstock (10), collecting the condensible vapors to give a first aqueous condensate (12), distilling the first aqueous condensate (14), collecting a HAA enriched second condensate (16) and precipitating HAA therefrom (18).

Pyrolysis is a general term for the thermal decomposition of any organic material including wood, plants, and fossil fuels. Thermal decomposition may occur either with the combustion of the feedstock or without the combustion of the feedstock. Pyrolysis with combustion normally uses the oxidation or burning of a portion of the organic material to provide the heat necessary to vaporize and decompose the bulk of the material. Pyrolysis without combustion uses heat supplied from an independent source in order to vaporize and decompose the organic material. Suitable heat sources include radiation, solid or gaseous heat carriers, or heated reactors and reactor walls.

Several methods of pyrolyzing a feedstock (10) are known to those skilled in the art. Suitable methods include both conventional and fast pyrolysis processes. A suitable conventional process is described in U.S. Pat. No. 3,106,473 to Hollenbeck. This process produces an aqueous condensate by extracting desirable smoke constituents generated by a partial combustion of hardwood sawdust into water. Preferably, the partial combustion occurs with limited access to air. Aqueous condensates produced by conventional processes typically have less than about 2% by weight HAA. If desired, the aqueous condensates may be concentrated by well known evaporation procedures before being used in the process of this invention.

Fast pyrolysis techniques also provide a product which may be used to practice this invention. Suitable fast pyrolysis procedures are described in U.S. Pat. No. 4,876,108 to Underwood et al. Fast pyrolysis rapidly heats a suitable feedstock to temperatures in excess of 400° C. in less than 2.0 seconds and then collects condensible vaporous constituents produced by the rapid heating. Preferably the rapid heating occurs in the absence of air in order to prevent oxidation of reactive constituents before they are collected. A suitable fast pyrolysis process generates products having between 1–35% by weight HAA. For example, an aqueous extract of a wood fast pyrolysis product containing about 50% organic solids is a suitable first condensate. In addition, an aqueous extract of a cellulose pyrolysis product is suitable. Another condensate may be obtained by pyrolyzing glucose or a glucose solution. A particular preferred condensate may be obtained by pyrolyzing a corn syrup solution.

The aqueous condensates (12) resulting from the pyrolysis of suitable feedstocks are made up of a complex and variable mixture of chemicals produced during pyrolysis. A preferred first condensate may be about 25°–30° Brix and contain about 5% by weight HAA. If desired, the solids content of an aqueous condensate may be increased to a desired concentration using well known evaporative methods. A preferred concentrated condensate may be about 50°–60° Brix. Evaporative methods which do not subject the aqueous condensate to elevated temperatures for extended periods of time are preferred because HAA degradation is minimized by such methods.

The distillation of the first condensate (14) is preferably performed under reduced pressure in order to keep the distillation temperature as low as possible which minimizes thermal losses of HAA due to degradation, subsequent reaction or decomposition. The vacuum provided by an aspirator is generally sufficient for performing the distillation, pressures of about −29 inches of mercury are sufficient. Similarly, it is important to keep the length of time a condensate is heated to elevated temperatures as short as possible. Both the temperature and the length of time a condensate is heated generate increased losses of HAA. For example, Table 1 illustrates the amount of degradation of HAA in a 45° Brix dextrose condensate or a 70° Brix wood condensate when the condensates were heated at varying temperatures for about thirteen hours.

TABLE 1

Degradation of HAA after 13 Hours at Various Temperatures

| Temperature °C. | 70° Brix from Wood | 45° Brix from Dextrose |
| --- | --- | --- |
| 25 | 0 | 0 |
| 60 | 10% | 10% |
| 70 | * | 25% |
| 90 | 90% | 60% |

*Not calculated

Three distillation parameters are critical to maximize yields of precipitated HAA:

1. The temperature of the stillpot should be low;
2. The time the stillpot is subject to elevated temperatures should be minimized;
3. The amount of water in the HAA enriched condensate is preferably below about 2% by weight in order for a homogenous solution to form when it is combined with methylene chloride. If the HAA enriched condensate contains more than about 2% water, two phases form when is combined with methylene chloride and HAA does note precipitated.

By using two batch distillations instead of one, the above three criteria may be successfully met. In the first distillation all the components of the starting feed up to and including the HAA rich fraction are distilled over in one fraction as quickly as possible to minimize the time the stillpot is at an elevated temperature. The high water content of this fraction (about 30–40%) prevents precipitation. A second distillation in which the water is distilled off and the water reduced still bottoms from this second distillation is the material that is HAA enriched.

Both batch type and continuous type distillations are useful for the recovery of HAA from pyrolysis mixtures. In fact, continuous type distillations offer the advantages of exposing the pyrolysis mixture to elevated temperatures for considerably shorter time periods (minutes rather than hours) that batch type distillations. The shorter the distillation time period, the less HAA that is lost to thermal breakdown. Continuous distillations such as wiped film evaporators, thin film evaporators, short path evaporators, and molecular stills have all been found useful in reducing distillation times.

When a wood condensate is distilled under reduced pressure, a typical second condensate (16) includes constituents which are normally liquid or water soluble at ambient temperatures. The principle organic constituent which is present in the second condensate at distillation temperatures between 20°–45° C. at about −29 inches of mercury is acetol although trace amounts of HAA are present in the second condensate at temperatures of about 25° C. and acetic acid, another major constituent, is present in the second condensate in significant percentages at temperatures between 30°–60° C. At temperatures between 45°–85° C., the second condensate is found to contain the greatest concentration of HAA and the fraction collected between 45°–85° C., and preferably between 60°–70° C., is used to precipitate HAA from the condensate using procedures described below. Although the concentration of HAA is enriched by vacuum distillation, fractions containing the greatest percentages of HAA are still contaminated with substantial quantities of other organic constituents depending on the type of feedstock and the method used to pyrolyze the feedstock.

To precipitate HAA (18), the HAA enriched second condensate is added to an organic solvent in a sufficient amount to give an homogeneous solution without causing a phase separation between the aqueous and organic portions of the solution. Preferably, sufficient methylene chloride is added to the second condensate to effect precipitation of HAA without forming two phases. The addition of an amount of methylene chloride which is sufficient to give a homogenous solution provides for HAA to slowly precipitate provided that the overall concentration of HAA in the homogenous solution is greater than about 2% by weight. If desired, the temperature of the homogeneous solution may be lowered in order to aid precipitation. Temperatures of −4° C. have been found to be useful for the precipitation process. The undesired organic constituents present in the second condensate remain solubilized in the methylene chloride/water solution and HAA may be recovered by simple filtration to separate the precipitated product and the undesired liquids. Any residual traces of undesired constituents may be removed by washing the precipitated HAA with fresh cold methylene chloride.

Other solvents or mixtures of solvents besides methylene chloride may be used to precipitate HAA from the HAA enriched second condensate. A suitable solvent, however, must be chosen to include a proper range of hydrogen bonding parameters and an appropriate polarity index in order to allow the HAA to precipitate but still solubilize the undesired organic constituents present in the second condensate. A suitable solvent must also be easy to separate from the precipitated HAA. One suitable alternative solvent is chloroform.

HAA may also precipitate directly from the second condensate enriched distillate when the HAA concentration is greater than about 40% by weight and the water content is less than about one percent by weight. The solid HAA which precipitates directly without mixing with another solvent may be readily filtered from the unwanted liquid and washed with methylene chloride to remove any undesired organic constituents present with the precipitated HAA.

Precipitated HAA produced by this invention may be used in a wide variety of applications in both the food and cosmetic industries. For example, many different meat sources such as beef, pork, lamb, poultry, and fish may be contacted with aqueous solutions of HAA to impart varying degrees of coloring or browning to the meat. Advantageously, any desired degree of browning may be developed without imparting strong or overpowering smoke flavors which are present in traditional liquid smoke products.

Aqueous HAA solutions of at least about 0.5-10% by weight of HAA may be prepared and applied to foodstuffs. Upon heating to typical foodstuff preparation temperatures, as obtained in a microwave oven for example, a desirable golden brown color is produced on the foodstuff.

Any well known application method including but not limited to atomizing, dipping, spraying, brushing, or soaking may be used to contact a foodstuff with an aqueous HAA solution. In addition, well known additives such as gums, thickeners, preservatives, or flavorings may be incorporated in the aqueous HAA solutions to produce browning and flavoring solutions most suitable for application to a particular type of foodstuff.

Although glucose has been used as a browning agent, the high temperatures required to obtain significant browning with glucose limits the usefulness of glucose as a browning agent. This is particularly important for microwave foodstuffs because actual preparation temperatures are not as high as traditional cooking and heating procedures. Therefore, to obtain suitable browning on foodstuffs prepared by microwave, it is preferable to form HAA by pyrolysis of a carbohydrate-containing foodstuff and then apply the HAA to a foodstuff. This enables the production of a more desirable golden brown color on the foodstuff at a lower temperature than is possible by direct application of glucose.

The ability of an aqueous HAA solution for coloring or browning protein may be demonstrated by a simple qualitative test. Briefly, a filter paper (Whatman #1, 7.5 cm) is soaked in an aqueous glycine solution (22 g glycine dissolved in 100 ml of phthalate buffer pH 5.5) and then dried. A drop of a dilute solution of HAA in water is applied to the dried filter paper, the paper is again dried and is then heated in an oven at 150° F. to allow the HAA to react with the glycine. The intensity of color increases approximately proportionally to the increase in HAA concentration. This test has shown aqueous HAA solutions as dilute as 0.1% by weight react with glycine to produce a visible brown color on the filter paper.

In addition, when the foodstuff is a meat product that does not contain nitrites the potential for undesired warmed over flavor (a common food processing concern) is greatly diminished. It is believed that Maillard reaction products which are typically produced by reactions between sugars and proteins are the principle agents which impart color and reduce warmed over flavors in foodstuffs. A widely accepted reaction mechanism for generating Maillard reaction products has been published by Hodge et al., *J. Am. Chem. Soc.* 75:316 (1953). Additional reaction mechanisms have been suggested by Mauron, *Prog. Food Nutr. Sci.,* 5:5 (1981) and Feather, *Prog. Food Nutr. Sci.,* 5:37 (1981). Briefly, the three principal stages of the reaction between sugars and proteins include: 1) formation of an aldosylamine between a sugar and a protein amino acid and rearrangement to a 1-amino-1-deoxy-2-ketose (amadori compound); 2) loss of the amino functionality from the amadori compound to form carbonyl intermediates through several pathways; and 3) strecker degradation of additional amino acids by reacting with the carbonyl intermediate produced in the above pathways to form aldehydes, ammonia, and carbon dioxide.

It has been suggested that the first step in the production of Maillard reaction products in foodstuffs containing glucose is the formation of a two carbon atom amino compound, particularly a 1,2-enaminol. Although the enaminol includes a two carbon atom fragment derived from glucose, it is doubtful that HAA is formed by glucose decomposition before reaction with an amino acid because temperatures of about 225° C. are required to initiate thermal glucose decomposition. In contrast, the presence of 1,2-enaminols can be detected when glucose and protein amino acids are reacted at much lower temperatures. This suggests that HAA is not an isolatable intermediate of the Maillard reaction.

Furthermore, warmed over flavors are also generally believed to be associated with uncontrolled oxidation of phospholipids. For example, Eichner, In *Autoxidation in Food and Biological Systems,* ed. M. G. Simic and M.

Karel, Plenum press, New York, p. 367 (1979) reported that the colorless intermediates of the Maillard reaction may be essential to the antioxidative effect need to reduce or eliminate warmed over flavor. Eichner concluded that the 1,2 enaminols and similar intermediates are the most important antioxidants and such intermediates appear to be derived from the reaction of HAA with amino acids.

Namiki, et al. *Prog. Food Nutr. Sci.,* 5:81, (1981) reported that electron paramagnetic resonance spectra sugar-amine compounds indicated that N,N-disubstituted pyrazine cation radicals were formed by reacting glucose and n-butylamine. These pyrazine radicals were believed to be the product of the reaction of a two carbon fragment derived from glucose that is formed by the degradation a glycosylamine initially formed by reacting glucose and proteinaceous amines. The two carbon enaminol fragment subsequently condenses with a second enaminol to give the reported pyrazine radical. The production of a HAA-amine derivative and the subsequent reaction of such a compound was postulated by Namiki, et al., however, they did not indicate that HAA was produced directly from the fragmentation of glucose as is the case in the pyrolytic decomposition of glucose.

The concentrations of HAA in an aqueous solution suitable to impart a rich golden brown color to meat when the meat is cooked in a microwave oven are listed in Table 2. An aqueous HAA solution may be applied to the surface of Swift Premium Brown and Serve Sausages by a 2 to 3 second dip. The dipped sausages are then microwaved for one minute along with untreated sausages which serve as controls. After microwaving, the sausages are evaluated for visual color appeal. Solutions having a HAA concentration as low as 0.05% impart a noticeable golden brown color to microwaved sausages.

TABLE 2

| HAA in Solution (Wt./vol. %) | Surface Coating Concentration ($\mu$g HAA/cm$^2$) | Total Product Loading ($\mu$g HAA/g product) | Color Description |
| --- | --- | --- | --- |
| 2.0 | 184 | 350 | Very Brown |
| 1.0 | 92 | 175 | Very Brown |
| 0.5 | 46 | 88 | Golden Brown |
| 0.1 | 9 | 18 | Light Golden Brown |
| 0.05 | 5 | 9 | Very Light Brown |
| 0 | 0 | 0 | Greyish White |

HAA = hydroxyacetaldehyde

A preferred process for browning foodstuffs or inhibiting warmed over flavor is to obtain HAA from a carbohydrate-containing feedstock and apply sufficient quantities of the HAA to the foodstuff to produce the desired result. The amount required and method of application will vary widely depending of the effect desired, the specific type of foodstuff and the particular conditions of preparing the foodstuff. To impart browning to a microwavable meat product, the application of about a 1–5% by weight aqueous HAA solution produces a desirable golden brown color to the meat.

In addition to direct application to a foodstuff, an aqueous HAA solution may also be applied to foodstuffs indirectly by applying the liquids to foodstuffs indirectly by applying the HAA solution to sausage and foodstuff casings. The indirect application to casings allows a processor to impart a brown color to a particular food stuff.

Any well known method may be used to contact the sausage or foodstuff casing with an aqueous HAA solution. See, for example, the methods disclosed in U.S. Pat. Nos. 3,330,669 and 4,504,500. Suitable methods for contacting foodstuff casing with an HAA solution are also described in U.S. patent application Ser. No. 07/416,963 filed Oct. 4, 1989, the relevant portions of which are incorporated herein by reference.

Food casings suitable for use with the present invention include tubular casings, and preferably tubular cellulosic casings, that are prepared by any of the methods well known in the art. Such casings are generally non-fibrous, flexible, thin-walled seamless casings formed of regenerated cellulose or cellulose ethers, such as hydroxyethyl cellulose, and having a variety of diameters. Tubular cellulosic casings having a fibrous reinforcing web embedded in the wall of the casings, commonly called fibrous food casings, are also suitable.

A HAA solution may be applied to the outer surface of the food casing by passing the casing through a bath of the HAA solution. The solution is generally allowed to soak into the casing for an amount of time sufficient for the casing to incorporate the desired amount of material into the casing, before doctoring off any excess solution by passing the casing through squeeze rolls or wipers. The solution may also be externally applied to the casing by methods other than dipping, such as spraying, brushing or roll-coating.

Another method of treating the casing with solution involves passing a flattened, tubular, cellulose sausage casing over guide rolls through a dip tank which contains the solution. The casing passes over additional guide rolls after exiting the dip tank, and then passes between squeeze rolls which minimize any excess carryover of the solution. The total contact time of the casing with the solution in the dip tank, and with excess solution on the casing passing over the guide rolls before the casing passes through the squeeze rolls, typically determines the amount of material that the casing will incorporate. The casing is then sent on to conventional further processing, including conventional humidification, as may be required, and conventional shirring.

Alternatively, a HAA solution may be applied to the internal surface of the casing by any of several well known procedures. These include slugging or bubble coating, spraying, and coating while shirring. The slugging method for coating the inside of a casing involves filling a portion of the casing with the solution, so that a "slug" generally resides at the bottom of a "U" shape formed by the casing, and then moving the continuous indefinite length of casing so that the "slug" remains confined within the casing, while the casing moves past the slug and is coated on its inside wall by the solution.

The casing may then be shirred by conventional methods or, before shirring, it may be dried or humidified to a desired water content suitable for shirring or further processing. The need for conventional drying or humidification after external treatment depends on the water content of the casing after treatment and the type of casing. If the casing is a non-fibrous casing, a water content within the range of about 8–18 wt. % water immediately before shirring is typical, and for fibrous casing a water content within the range of about 11–35 wt. % water immediately before shirring is typical, where weight percent is based on the total weight of casing including water.

An aqueous HAA solution is also a particularly preferred when used with collagen casings because HAA is difunctional and thus is an effective cross-linking agent. The physical properties of the collagen casings may be improved by the cross-linking provided by hydroxyacetaldehyde.

HAA may also be used in the cosmetic industry as an active ingredient in artificial skin tanning products including liquids, lotions, creams and gels. Conventional artificial skin tanning preparations use dihydroxyacetone as the active ingredient to impart a colored or brown color to skin. Dihydroxyacetone, however, may impart a yellow-orange tone to the skin and has been associated with mutagenic properties in lab tests. HAA may be used alone or as a supplemental browning agent in artificial skin tanning preparations.

A wide variety of food flavors may be produced by combining various amino acids with HAA. (For example, aqueous sample solutions were made comprising 0.1 wt/vol. % amino acid and 0.1 wt/vol. % HAA. The samples were heated in an autoclave at 121° C. for two hours and then cooled to room temperature. The samples were then evaluated for aroma and physical appearance. The results that were obtained are illustrated in Table 3.

TABLE 3

| AMINO ACID | AROMA | PHYSICAL APPEARANCE |
|---|---|---|
| Alanine | Fruity, Alcoholic | Dark, Clear, No PPT |
| Histidine | Roast Beef | Dark, cloudy, slight PPT |
| Glycine | Roasted, Nutty | Dark, No PPT |
| Arginine | Dry, Musty | Light Red, No PPT |
| Lysine | Bread, Bakerylike | Dark, No PPT |
| Glutamic Acid | Sugary, Sweet | Dark, Hazy, Slight PPT |
| Methionine | Cabbage, Sauerkraut | Light Red, Slight PPT |

(Amino acids from Aldrich Chemical Company, Milwaukee, Wisconsin).

Figure 1:
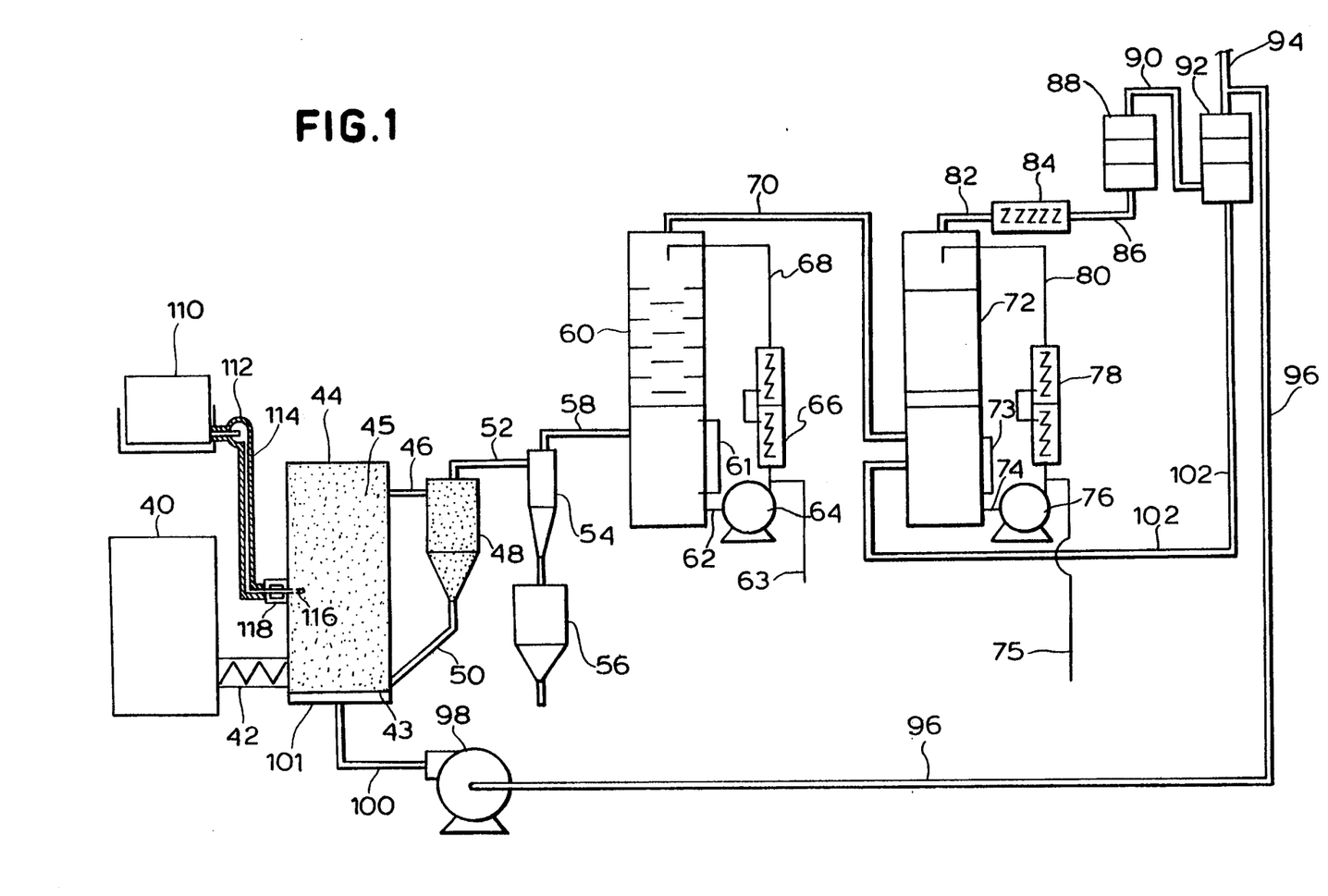
FIG. 1 schematically represents a fast pyrolysis apparatus including an upflow reactor, and FIG. 2 schematically illustrates a process to isolate HAA.

FIG. 1 illustrates an apparatus which may be used for the fast pyrolysis of carbohydrate-containing feedstock by a rapid thermal process. Bin (40) stores a supply of the feedstock in granular or powder form. The feedstock is removed from the bin (40) by an auger (42) and fed to the lower interior portion of the reactor (44) above a windbox (101) and a grid plate (43). The auger (42) may be water cooled at the inlet to the reactor to prevent premature pyrolysis, which can produce tarry materials.

Alternatively, a solution or syrup of a carbohydrate-containing liquid feedstock may be injected into the reactor using a suitable well known injector apparatus. Heated storage tank (110) stores a supply of a liquid feedstock. The liquid feedstock is pumped from the storage tank (110) by a pump 112 through a steam jacketed conduit (114). The liquid feedstock enters the reactor (44) through an injector nozzle (116). The injector nozzle (116) may be cooled at the inlet to the reactor by a water-cooled jacket (118) to prevent premature pyrolysis of the liquid feedstock in the injector nozzle. A stream of recirculation gas transport fluid is fed by a conduit (100) into the windbox (101), through the grid plate (43) and into the lower portion of the reactor (44) containing a heat transfer medium such as sand (45). Rapid mixing and conductive heat transfer from the sand (45) to the sugar or starch feedstock occurs in the reactor (44). Pyrolytic conversion of the feedstock to a raw product vapor is initiated and continues through the reactor with upward flow into the primary cyclone separator (48). The pyrolysis stream comprising sand (45) and pyrolysis vapor is removed from the reactor (44) by conduit (46) and fed to primary cyclone separator (48). The hot sand (45) is removed from the product vapor stream in the separator (48) and recycled by means of a conduit (50) to the reactor (44). The recycled sand (45) is reintroduced into the lower portion of the reactor (44) at a point above the grid plate (43). Product vapor containing char is withdrawn from the primary cyclone separator (48) by a conduit (52) and fed to a secondary cyclone separator (54) which can be a high efficiency reverse flow cyclone separator. Char and solid sand fines are removed in the secondary cyclone and fed therefrom to a char catchpot (56) for disposal or further handling as desired.

The hot product stream is withdrawn from the top of the secondary separator (54) through a conduit (58) which feeds the vapor comprising condensible and non-condensible constituents and some fine residual char and ash to the lower interior space of a baffled condenser (60) where the vapor is immediately quenched. The condenser (60) uses the product liquid as the quench medium.

The condensed liquid product is withdrawn from the bottom of the condenser (60) through a conduit (62) and is fed to a pump (64) which pumps it to a heat exchanger (66) indirectly cooled by water. The cooled product liquid is removed from the heat exchanger (66) and returned by conduit (68) to the top of the condenser (60) as a spray. A conventional transparent vertical sight indicator (61) is mounted on the lower part of the first condenser (60). The sight indicator has high and low liquid level marks. When the volume of liquid in the condenser (60) reaches the high level mark raw pyrolysis liquid is withdrawn through a conduit (63) until the liquid level reaches the low level mark. Liquid is then accumulated in the condenser until it again reaches the high level mark and the raw pyrolysis liquid withdrawal step is repeated.

Non-condensed product vapor is withdrawn from the top of the condenser (60) by conduit (70) and is fed to a packed second condenser column (72) where it is further cooled. Liquid is withdrawn by a conduit (74) from the bottom of the packed second condenser and fed to a pump (76) which pumps it through a water cooled heat exchanger (78). Cooled liquid product is removed from the heat exchanger (78) by conduit (80) and is fed to the top of the packed second condenser column (72). A conventional transparent vertical sight indicator (73) is mounted on the lower part of the second condenser (72). The sight indicator has high and low liquid level marks. When the high level mark is reached raw pyrolysis liquid is withdrawn through conduit (75) until the liquid level reaches the low mark.

A vapor stream is removed from the top of the packed second condenser column (72) by a conduit (82) and fed through a water cooled heat exchanger (84) from which it is fed to a conduit (86) which feeds it to a mist eliminator (88). The vapor is fed from the mist eliminator (88) to a conduit (90) which delivers the vapor to a filter (92). Liquid is removed from the bottom of the filter (92) by means of a conduit (102) and recirculated to the bottom portion of the second condenser column (72) above the level of liquid in the column. A portion of the resulting clean by-product gas stream is ducted from the filter (92) by a conduit (94) and fed to conduit (96) which feeds it to a gas recirculation blower (98). The recirculated gas is fed from the blower (98) to a conduit (100) which feeds it into the bottom of the reactor (44).

The following examples are provided to further illustrate specific aspects and practices of this invention. These examples describe particular embodiments of the invention, but are not to be construed as limitations on the appended claims. Example 1 describes the distillation of pyrolysis condensates, Example 2 describes precipitating HAA, Example 3 describes coloring or browning a foodstuff, Example 4 describes using HAA in a skin tanning product, Example 5 describes using HAA to inhibit warmed over flavor in a foodstuff and Example 6 describes a multiple distillation process.

In the examples, the concentration values for the organic components in the described liquids are given as °Brix values. The °Brix values were obtained using standard refractory techniques which are well known in the sugar industry. The percent weight per volume (% wt./vol.) values for HAA were obtained using gas chromatography and comparing the peak integrations of a sample of a liquid (diluted if necessary) with peak integrations of a standard curve generated from a 1–5% serial dilution of hydroxyacetaldehyde in water. Gas chromatograms were run on a Varian Gas Chromatograph (Model 3300 equipped with a Varian Integrater Model 4290) fitted with a fused-silica capillary column (0.25 mm × 30 m J&W DB-Wax column) using hydrogen carrier gas at a flow rate of 2.0 ml/mm and a temperature program of 40° C. initial temperature, zero minute hold followed by increasing the temperature at 8.0° C./minute to 255° C. The injector temperature was 220° C., the detector temperature was 300° C.

Under these conditions, the retention time of HAA in the J&W DB-Wax column was 4.70 minutes.

EXAMPLE 1

This example provides the distillation profiles of different pyrolysis condensates. The three pyrolysis products are a raw fast pyrolysis condensate, a 50 brix aqueous extract of a fast pyrolysis condensate, and a 55 Brix liquid smoke solution, CHARSOL SUPREME ® (Red Arrow Products Co. Inc., Manitowoc, Wis.).

Two liters of each of the pyrolysis condensates were distilled under a vacuum (−29 inches of mercury) using a Snyder distilling column (Ace Glass, Incorporated, Vineland, N.J.). Distillation fractions were collected every 5° C. between 20°–90° C. These fractions were analyzed by gas chromatography for percentages of the following organic compounds: HAA, acetic acid, acetol, and cyclotene. The results of the gas chromatography analysis for each fraction collected from the three pyrolysis condensates are shown in Tables 4–6. The greatest yield of desired hydroxyacetaldehyde was obtained from the distillation of a 50° Brix aqueous extract of a fast pyrolysis condensate.

TABLE 4

DISTILLATION OF WOOD FAST PYROLYSIS CONDENSATE (2000 ml)

| Temp. °C. | Mass (g.) | % HAA | % AA | % AC | % CT |
|---|---|---|---|---|---|
| 20–25 | 552.0 | <0.1 | 6.6 | 1.7 | <0.1 |
| 25–30 | 130.2 | 0.3 | 15.5 | 5.0 | <0.1 |
| 30–35 | 45.8 | 2.4 | 22.1 | 8.0 | <0.1 |
| 35–40 | 23.9 | 3.3 | 26.3 | 11.4 | <0.1 |
| 40–45 | 30.1 | 8.1 | 27.2 | 15.6 | <0.1 |
| 45–50 | 19.6 | 12.0 | 26.7 | 16.4 | <0.1 |
| 50–55 | 22.8 | 16.2 | 23.6 | 14.2 | <0.1 |
| 55–60 | 27.1 | 20.4 | 20.6 | 14.0 | <0.1 |
| 60–65 | 50.0 | 21.9 | 14.0 | 12.5 | 0.3 |
| 65–70 | 83.0 | 20.7 | 8.6 | 6.4 | 0.7 |
| 70–75 | 54.8 | 6.9 | 6.0 | 2.4 | 2.0 |
| 75–80 | 35.4 | 3.3 | 4.7 | 1.4 | 3.6 |
| 80–85 | 19.1 | 3.0 | 4.0 | 1.3 | 3.4 |
| 85–90 | 17.3 | 2.7 | 3.6 | 1.2 | 2.6 |

Percentages are from G.C. analysis
HAA—Hydroxyacetaldehyde
AA—Acetic Acid
AC—Acetol
CT—Cyclotene

TABLE 5

DISTILLATION OF CONCENTRATED AQUEOUS WOOD CONDENSATE (50° BRIX, 2000 ml)

| Temp. °C. | Mass (g.) | % HAA | % AA | % AC | % CT |
|---|---|---|---|---|---|
| 20–25 | 810.1 | 0.3 | 15.4 | 5.3 | <0.1 |
| 25–30 | 74.1 | 0.9 | 29.2 | 13.1 | <0.1 |
| 30–35 | 40.3 | 1.8 | 35.5 | 21.5 | <0.1 |
| 35–40 | 10.8 | 4.5 | 32.8 | 29.1 | <0.1 |
| 40–45 | 12.0 | 7.5 | 27.5 | 32.7 | <0.1 |
| 45–50 | 23.9 | 11.1 | 23.1 | 35.6 | <0.1 |
| 50–55 | 21.8 | 18.9 | 18.9 | 35.3 | <0.1 |
| 55–60 | 155.8 | 19.2 | 12.7 | 23.2 | 0.5 |
| 60–65 | 84.6 | 72.6 | 0.8 | 8.7 | 1.4 |
| 65–70 | 17.4 | 44.4 | 0.2 | 4.1 | 2.4 |
| 70–75 | 43.4 | 36.9 | <0.1 | 3.1 | 4.2 |
| 75–80 | 7.7 | 33.3 | <0.1 | 2.2 | 5.5 |
| 80–85 | 8.0 | 18.3 | <0.1 | 0.9 | 7.0 |
| 85–90 | 9.3 | 11.7 | <0.1 | 0.7 | 16.9 |

Percentages are from G.C. analysis
HAA—Hydroxyacetaldehyde
AA—Acetic Acid
AC—Acetol
CT—Cyclotene

TABLE 6

DISTILLATION OF CHARSOL SUPREME ® (500 BRIX, 2000 ml)

| Temp. °C. | Mass (g.) | % HAA | % AA | % AC | % CT |
|---|---|---|---|---|---|
| 20–25 | 522.2 | <0.1 | 10.4 | 2.1 | <0.1 |
| 25–30 | 289.2 | <0.1 | 24.2 | 7.0 | <0.1 |
| 30–35 | 54.8 | 2.7 | 37.4 | 17.5 | <0.1 |
| 35–40 | 35.8 | 6.0 | 35.3 | 18.6 | <0.1 |
| 40–45 | 46.5 | 11.1 | 29.2 | 19.5 | <0.1 |
| 45–50 | 24.0 | 16.8 | 22.6 | 18.6 | 0.1 |
| 50–55 | 44.6 | 23.4 | 19.2 | 17.2 | 0.4 |
| 55–60 | 43.4 | 16.5 | 7.3 | 8.5 | 0.7 |
| 60–65 | 29.0 | 15.6 | 5.6 | 4.9 | 1.7 |
| 65–70 | 11.1 | 5.7 | 4.4 | 2.6 | 2.6 |
| 70–75 | 22.5 | 6.0 | 3.0 | 1.5 | 9.9 |
| 75–80 | 48.1 | 3.3 | 1.9 | 0.7 | 13.4 |
| 80–85 | 8.2 | 4.2 | 2.0 | 0.8 | 16.0 |
| 85–90 | 9.6 | 2.7 | 2.0 | 0.7 | 19.3 |

Percentages are from G.C. analysis
HAA—Hydroxyacetaldehyde
AA—Acetic Acid
AC—Acetol
CT—Cyclotene

EXAMPLE 2

This example illustrates specific conditions to precipitate hydroxyacetaldehyde.

The data in Table 7 indicate that a distillation fraction condensate (DFC) of greater than about 20% by weight HAA and less than about 2% water is needed for HAA to precipitate from a 10:1 vol/vol methylene chloride: DFC mixture. At concentrations greater than about 40% by weight HAA and at most about 1% water, HAA precipitates from the DFC at ambient temperatures without the addition of methylene chloride.

TABLE 7

HAA PRECIPITATION CONDITIONS

| Distillation Fraction Temp. (°C.) | % HAA in DFC | % Water in DFC | HAA Precipitate |
|---|---|---|---|
| 40–45 | 7.5 | 10.8 | NO |
| 45–50 | 11.1 | 7.0 | NO |
| 50–55 | 18.9 | 3.1 | YES |
| 55–60 | 19.2 | 1.0 | YES |
| 60–65 | 72.6 | 1.0 | YES* |
| 65–70 | 44.4 | 1.0 | YES* |
| 70–75 | 36.9 | 1.0 | YES |
| 75–80 | 33.3 | 1.0 | YES |
| 80–85 | 18.3 | 1.0 | NO |
| 85–90 | 11.7 | 1.0 | NO |

(1 gram of DFC was added to 10 ml of methylene chloride and stirred at −4° C. for about 24 hours)
*HAA precipitation occurred both with and without added methylene chloride.

The data in Table 8 illustrates the dilution conditions for precipitation of HAA from a DFC containing 19.2% by weight HAA and about 1% by weight water. Two grams of the DFC were added to test tubes with various amounts of methylene chloride and cooled while stirring to −4° C. overnight.

TABLE 8

HAA PRECIPITATION CONDITIONS

| Sample | DFC (g)/ CH$_2$Cl$_2$ (ml) | HAA Precipitate |
|---|---|---|
| 1 | 2/1 | NO |
| 2 | 1/1 | NO |
| 3 | 1/2 | NO |
| 4 | 1/3 | NO |
| 5 | 1/4 | YES |
| 6 | 1/5 | YES |
| 7 | 1/6 | YES |
| 8 | 2/15 | YES |
| 9 | 1/10 | YES |
| 10 | 2/25 | NO |
| 11 | 1/15 | NO |
| 12 | 1/20 | NO |

This table identifies two parameters for successful HAA precipitation. First, the ratio of methylene chloride to DFC must be at least about 3:1 in order to effect HAA precipitation. Second, the ratio of methylene chloride to DFC must be below a critical value such that the final HAA concentration in the combined methylene chloride-DFC mixture is above about 2% HAA.

The maximum amount of water that can be present in a DFC in order for HAA to precipitate when mixed with a ten fold excess of methylene chloride was determined using a DFC containing about 50% by weight of HAA and about 2% by weight water. Different samples were spiked with additional amounts of water and one gram of each sample was added to ten ml of methylene chloride. The samples were stirred at −4° C. overnight. The results obtained are listed in Table 9.

TABLE 9

| SAMPLE | % WATER ADDED | TOTAL % WATER | HAA PRECIPITATE |
|---|---|---|---|
| 1 | 0 | 2 | YES |
| 2 | 1 | 3 | YES |
| 3 | 2 | 4 | YES |
| 4 | 3 | 5 | YES |

TABLE 9-continued

| SAMPLE | % WATER ADDED | TOTAL % WATER | HAA PRECIPITATE |
|---|---|---|---|
| 5 | 4 | 6 | YES |
| 6 | 5 | 7 | NO |
| 7 | 6 | 8 | NO |
| 8 | 7 | 9 | NO |
| 9 | 8 | 10 | NO |
| 10 | 9 | 11 | NO |

The data indicate a DFC may contain a maximum of about 6% water and still precipitate HAA when a ten fold excess of methylene chloride is used.

The water to methylene chloride ratio is critical for HAA precipitation to occur as shown in the next experiment. Table 10 lists the minimum amount of methylene chloride needed to precipitate HAA from a DFC containing about 50% HAA and about 2% water that was spiked with 0, 1, 2, and 3% added water. One gram of each sample was added to various amounts of methylene chloride and stirred at −4° C. overnight. The following results were obtained.

TABLE 10

| MLS METHYLENE CHLORIDE | HAA PRECIPITATE | | | |
|---|---|---|---|---|
| | DFC 2% WATER | DFC 3% WATER | DFC 4% WATER | DFC 5% WATER |
| 1 | NO | NO | NO | NO |
| 2 | NO | NO | NO | NO |
| 3 | NO | NO | NO | NO |
| 4 | YES | YES | NO | NO |
| 5 | YES | YES | NO | NO |
| 6 | YES | YES | YES | NO |
| 7 | YES | YES | YES | NO |
| 8 | YES | YES | YES | NO |
| 9 | YES | YES | YES | NO |
| 10 | YES | YES | YES | YES |
| 11 | YES | YES | YES | YES |
| 12 | YES | YES | YES | YES |

In order for HAA to precipitate the level of water in the DFC must be low enough so that a homogenous solution forms when the DFC is mixed with the methylene chloride. If too much water is present in the DFC then two phases form when the DFC is added to methylene chloride because the solubility of water in methylene is only about 1%. When two phases form, the HAA stays in the top aqueous phase as a syrup and does not precipitate out. Adding enough excess methylene chloride until the two phase mixture becomes one phase, however only works up to a point. If the addition of excess methylene chloride to solubilize all of the water in a DFC (to effect one homogenous phase) lowers the HAA concentration in the combined mixture below about 2%, no HAA will precipitate, even if the mixed is homogenous.

EXAMPLE 3

This example shows the capability of an aqueous HAA solution to brown proteinaceous foodstuffs. Precipitated HAA was dissolved in an amount of water sufficient to give a 2.0 wt./vol. % solution. This aqueous HAA solution was coated on pieces of white string cheese and on raw ground beef. The coated string cheese and ground beef were then microwaved for three minutes. Both the coated string cheese and ground beef turned a dark brown smoked color. Uncoated string cheese and ground beef were used as controls and did not change color when microwaved.

Two extruded, raw, uncooked and untreated hot dogs (Chermak Sausage Company, Manitowoc, Wis.) were wrapped in a cellulose casing material. One hot dog was dipped in an aqueous solution of 5% acetic acid, 1% xanthan gum, and 1% HAA. The other hot dog was dipped in an aqueous solution of 5% acetic acid and 1% xanthan gum and served as a control. Both hot dogs were placed in the respective solutions for 45 seconds and then both hot dogs were heated in an oven which cooked the hot dogs according to the following program: 110° F. for 10 minutes, 140° F. for 45 minutes, 160° F. for 15 minutes, and 180° F. for 10 minutes. After cooking, both hot dogs were rinsed thoroughly in cold water and then the outer casing was removed. The hot dog treated with the solution containing 1% HAA had developed a brown smoked color compared to the untreated hot dog that had a light red cured color. Both hot dogs were essentially equivalent in flavor.

Mixtures of HAA with other carbonyl compounds may also be used to impart brown color to a foodstuff. For example, the microwave browning capability of HAA, 1,3-dihydroxyacetone, and glucose in aqueous solutions. Five percent solutions of mixtures listed below were applied to the surface of the sausages of example 9 by dipping the sausages for about 2 seconds into each solution. The sausages were then heated in a microwave for about one minute along with non-treated sausages as controls. The following results were obtained.

| Solution | Sausage Color |
| --- | --- |
| 5% HAA | Rich, golden brown |
| 5% 1,3-dihydroxyacetone | Slightly brown |
| 5% Glucose | No color |
| 5% HAA + 5% glucose | Rich, golden but not darker than just 5% hydroxyacetaldehyde |
| No Smoke Control | No Color |

EXAMPLE 4

This example shows the capability of precipitated HAA to artificially tan skin. An amount of moisturizing hand cream, Jergens EVERSOFT ® (The Jergens Skin Care Laboratories) and a sufficient amount of HAA were combined to provide a 8.0 wt./vol. % mixture. A portion of the mixture was applied to the skin of human test subjects along with a portion of the moisturizing hand cream without added HAA. In each case the mixture containing the HAA turned the subject's skin a dark tan color compared to the control which had no color change.

The skin tanning ability of HAA isolated by the method was compared to 1,3-dihydroxyacetone (a commonly used active ingredient in artificial skin tanning lotions). HAA and 1,3-dihydroxyacetone were each combined with a skincare lotion, Jergens EVER-SOFT ® (The Jergens Skin Care Laboratories) to provide two 5.0 wt./vol. % mixtures. A portion of each mixture was applied to the skin of human test subjects. In each case, the mixture containing HAA turned the skin a golden tan color as where the 1,3-dihydroxyacetone mixture turned the skin an orange-red color. Additional mixtures were also made to provide 2.5 wt./vol. % of each compound in the skin lotion described above. The color produced by the mixture on the skin of human test subjects was observed to be superior to either compound alone in both the intensity and the goldeness of the color imparted to the skin.

EXAMPLE 5

This example shows the ability of an aqueous HAA solution to inhibit warmed over flavor in meat. Lean turkey thigh meat was ground two times through a ⅛ inch plate on in commercial meat grinder. Two samples (100 g) were treated with 1500 ppm and 15,000 ppm HAA, respectively, which had been isolated from a fat pyrolysis wood condensate. Both samples were placed in 500 ml Erlenmeyer flasks and then heated in a boiling water bath until an internal temperature of 70° C. was reached. The flasks were then covered and placed in a cooler at 4° C. for 48 hours. After storage, both samples were evaluated for warmed over flavor by a taste panel.

The organoleptic evaluation was done by comparing a freshly cooked sample which had not been subjected to storage to the treated samples. The fresh control was cooked by bringing the internal temperature to 70° C. in a boiling water bath. The treated samples were also brought to 70° C. Eight panelists were asked to taste the samples and assign each with a numerical value between 1 and 5 with 5 having the least amount of warmed over flavor, panelists were instructed that the fresh control had a value of 5. The average values obtained are illustrated in Table 11.

TABLE 11

| Sample | Taste Panel Average Value |
| --- | --- |
| Fresh Control | 5.00 |
| No added HAA | 1.75 |
| 1500 ppm HAA | 3.12 |
| 15,000 ppm HAA | 3.25 |

The data show significant inhibition of warmed over flavor by an HAA solution. The taste panel values indicate a positive dose response correlation between the flavor of meat sample and the amount of HAA added to the meat sample.

EXAMPLE 6

This example shows a multiple distillation process useful to isolate hydroxyacetaldehyde from pyrolyzed wood.

Hardwood sawdust (available from Kretz Lumber Co. Inc., Antigo, Wis.) having a moisture content of about 10 wt. % is augered into a rapid thermal processing reactor (designed by Ensyn Technologies Inc, Gloucester Ontario, Canada) at a rate of about 2,000 lbs. an hour. The rapid thermal processing reactor is configured as described earlier in the specification on pages 18–21, with the exception that the recirculating sand used as the heat transfer medium is directly heated by a gas burner located in the windbox. The hardwood sawdust is heated in the reactor to a temperature of about 550° through contact with recirculating sand. At this temperature, the hardwood is vaporized to produce about 1440 lbs. of condensible vapor, 260 lbs. of non-condensible gas, and 300 lbs. of char and other solids.

The vapors produced from the hardwood sawdust are contained in the reactor for about 0.5 seconds as the vapors are transported to a condenser. In the condenser, the pyrolysis vapors are condensed in two circulating cold water heat exchangers in series through contact with cold recirculating liquid maintained at a temperature of about 45° F. to give a first aqueous condensate.

After collecting about 1000 gallons of the first condensate having a hydroxyacetaldehyde content of about 7 wt % the first condensate is transferred to a steam jacketed holding tank and diluted with about 700 gallons of water. The diluted pyrolysis liquid is heated to a temperature of 170° F. and stirred for two hours.

After heating in the holding tank, the diluted pyrolysis liquid is cooled to ambient temperature and allowed to separate into two phases, 1300 gallons of a second aqueous condensate which is a water-soluble organic phase containing about 30 wt. % organic solids including, in part, about 6.4 wt. % hydroxyacetaldehyde and 400 gallons of a water-insoluble phase. The water-insoluble phase is withdrawn from the holding tank and the water-soluble organic phase is transported at a rate of about 200 gallons/hr to a plate evaporator (manufactured by APV Crepaco Inc, Tonawarden, N.Y.) operating at a temperature of about 100° F. under a reduced pressure of 27 inches Hg. The water-soluble organic phase is concentrated about threefold in the plate evaporator to give a concentrated aqueous liquid containing about 70 wt. % organic solids, including, in part, about 15 wt. % hydroxyacetaldehyde.

The concentrated liquid is then transported to a steam jacketed, twenty-five square feet, wiped film evaporator (manufactured by Pfandler Engineered Systems, Rochester, N.Y.) at a rate of about 500 lbs/hr. The wiped film evaporator is operated at a temperature of about 400° F. under a reduced pressure of about 100 mm Hg. About 55 wt. % of the concentrated liquid is vaporized to give a second condensible vaporous product. The concentration of hydroxyacetaldehyde in the second condensible vaporous product is about 30 wt. %.

The second condensible vaporous product is transported under reduced pressure as a vapor from the wipe film evaporator into the middle of a first fractionation column (26'×2.0' packed column). The columnn is equipped with a closed loop reboiler on the bottom of the column and a condenser on the top that is filled with a timed reflux splitter. In the first fractionation column, the second condensible vaporous product is separated into two fractions; a first low boiling fraction containing less than about 0.5 wt. % hydroxyacetaldehyde with water, acetic acid and acetol being major components and a first high boiling fraction containing about 60 wt. % hydroxyacetaldehyde as a major component. The first low boiling fraction which accounts for about 50 wt. % of the second condensible vaporous product is removed from the top of the first column. The remaining 50 wt. % fraction recirculating in the reboiler is transferred to a second fractionation column.

The first high boiling fraction containing about 60 wt. % hydroxyacetaldehyde and less than 2 wt. % water is removed from the bottom of the first fractionation column, transported into a closed loop reboiler heated to a temperature of about 250° F. to give a third condensible vaporous product and then introduced under reduced pressure into the middle of a second fractionation column (26'×1.5' packed column) equipped with a closed loop reboiler on the bottom of the column and a condenser at the top that is filled with a timed reflux splitter. A desired enriched second low boiling fraction comprising about 80 wt. % of the first high boiling fraction and included about 75 wt. % hydroxyacetaldehyde is removed from the top of the second fractionation column and condensed in a heat exchanger that is maintained at a temperature of about 75° F. When condensed, the second lowing boiling fraction contains about 75 wt. % hydroxy acetaldehyde and less than about 2.4 wt. % water and is transported to a storage tank.

About 100 gallons of the condensed second low boiling fraction collected from the second fractionation column is then diluted with about 500 gallons of food grade methylene chloride to give a homogeneous solution. The homogeneous solution is cooled to about 35° F. for about forty-eight hours to give crystalline hydroxyacetaldehyde which is separated by filtration from the methylene chloride solution.

If desired, enough water may be added to the solid hydroxyacetaldehyde in the storage tank to dissolve the crystals and make an aqueous solution that is about 5 wt. % in hydroxyacetaldehyde. This solution may then be passed through a vacuum stripping column maintained at a temperature of about 150° F. under a reduced pressure of about 100 mm Hg to reduce the residual methylene chloride level to less than five ppm. The resulting solution of about 5 wt. % hydroxyacetaldehyde is then ready to be used in food applications.

We claim:

1. A method of browning a foodstuff without imparting a smoke flavor to the foodstuff comprising:
    contacting the foodstuff with a nonsmoke flavored aqueous solution containing precipitated hydroxyacetaldehyde.

2. The method of claim 1 wherein the hydroxyacetaldehyde is isolated from a pyrolyzed carbohydrate-containing feedstock.

3. The method of claim 2 wherein the feedstock is wood.

4. The method of claim 2 wherein the feedstock is cellulose.

5. The method of claim 2 wherein the feedstock is sugar.

6. The method of claim 2 wherein the feedstock is starch.

7. A method of claim 1 wherein the nonsmoke flavored aqueous solution comprises about 0.01–20 wt. % hydroxyacetaldehyde.

8. A method of claim 7 wherein the nonsmoke flavored aqueous solution comprises about 1–10 wt. % hydroxyacetaldehyde.

9. The method of claim 1 wherein the foodstuff is selected from the group consisting of cheese, beef, pork, lamb, an encased food product, poultry and fish.

10. The method of claim 9 wherein the encased food product is encased in a cellulose casing.

11. The method of claim 9 wherein the encased food product is encased in a collagen casing.

12. The method of claim 9 wherein the encased food product is a sausage.

13. A method for browning a foodstuff comprising:
    a) contacting the foodstuff with an nonsmoke flavored aqueous solution containing hydroxyacetaldehyde to give a treated foodstuff; and
    b) heating the treated foodstuff in a microwave for a length of time sufficient to impart a brown color to the foodstuff.

14. The method of claim 13 wherein the foodstuff is selected from the group consisting of cheese, beef, pork, lamb, poultry, fish, an encased food product, bakery goods and potatoes.

15. The method of claim 14 wherein the encased food product is a sausage.

16. A method of imparting enhanced browning to a foodstuff to be treated with a mild smoke flavor solution comprising:

adding hydroxyacetaldehyde to the mild smoke flavor solution to supplement the browning capability of the solution; and contacting the foodstuff with the resulting supplemented solution.

17. A method of imparting a mild smoke flavor to a foodstuff while also imparting an enhanced browning to the foodstuff comprising:

contacting the foodstuff with a mild smoke flavor solution; and contacting the foodstuff with a supplemental amount of hydroxyacetaldehyde sufficient to brown the foodstuff.

* * * * *

UNITED STATES PATENT AND TRADEMARK OFFICE
CERTIFICATE OF CORRECTION

PATENT NO. : 5,393,542  Page 1 of 2
DATED : February 28, 1995
INVENTOR(S) : JOHN A. STRADAL ET AL.

It is certified that error appears in the above-indentified patent and that said Letters Patent is hereby corrected as shown below:

Column 4, line 19, please delete "of".

Column 6, line 19, "homogenous" should be --homogeneous--.

Column 6, line 22, please delete "is".

Column 6, line 23, "note" should be --not--.

Column 6, line 42, "that" should be --than--

Column 7, line 5, "an homogeneous" should be --a homogeneous--.

Column 7, line 11, "homogenous" should be --homogeneous--.

Column 7, line 13, "homogenous" should be --homogeneous--.

Column 9, line 1, "press" should be --Press--.

Column 9, line 5, "1,2 enaminols" should be --1,2-enaminols--.

Column 9, line 16, "degradation a" should be --degradation of a--.

Column 11, line 18, please delete "(".

Column 11, line 56, "pump 112" should be --pump (112)--.

Column 14, line 43, "500 Brix" should be --50° Brix--.

Column 16, line 54, "mixed" should be --mixture--.

UNITED STATES PATENT AND TRADEMARK OFFICE
CERTIFICATE OF CORRECTION

PATENT NO. : 5,393,542
DATED : February 28, 1995
INVENTOR(S) : JOHN A. STRADAL ET AL.

It is certified that error appears in the above-indentified patent and that said Letters Patent is hereby corrected as shown below:

Column 16, line 55, "homogenous" should be --homogeneous--.

Column 18, line 8, "plate on in" should be --plate on a--.

Column 19, line 3, "7 wt % the" should be --7 wt.%, the--.

Column 19, line 37, "columnn" should be --column--.

Column 20, line 1, "hydroxy acetaldehyde" should be --hydroxyacetaldehyde--.

Column 20, line 40, "A method" should be --The method--.

Column 20, line 43, "A method" should be --The method--.

Column 20, line 57, "with an nonsmoke" should be --with a nonsmoke--.

Signed and Sealed this

Twenty-seventh Day of June, 1995

Attest:

BRUCE LEHMAN

*Attesting Officer*     *Commissioner of Patents and Trademarks*